United States Patent [19]
Bright et al.

[11] Patent Number: 5,781,272
[45] Date of Patent: Jul. 14, 1998

[54] EYESIGHT PROTECTION APPARATUS WITH ATTACHED EARPLUGS

[75] Inventors: Aaron Lee Bright; Robert W. Green. both of Memphis, Tenn.

[73] Assignee: Safety+Plus, Inc., Memphis, Tenn.

[21] Appl. No.: 870,433

[22] Filed: Jun. 6, 1997

[51] Int. Cl.$^6$ .................. G02C 5/20; G02C 1/00; G02C 5/14
[52] U.S. Cl. .............. 351/123; 351/118; 351/121; 351/158
[58] Field of Search ................ 351/158, 41, 123; 351/111, 156, 157, 118, 119; 128/864, 857; 602/74

[56] References Cited

U.S. PATENT DOCUMENTS

| | | | |
|---|---|---|---|
| 3,384,903 | 5/1968 | Malcom, Jr. | 2/14 |
| 3,620,608 | 11/1971 | Davis | 5/14 |
| 3,943,925 | 3/1976 | Leight . | |
| 4,153,348 | 5/1979 | Walters et al. | 5/20 |
| 4,632,104 | 12/1986 | Conrow | 128/864 |
| 4,671,265 | 6/1987 | Andersson | 11/2 |
| 4,848,892 | 7/1989 | Sonthonnax | 5/20 |
| 4,955,708 | 9/1990 | Kahaney | 7/10 |
| 5,074,375 | 12/1991 | Grozil | 7/2 |
| 5,475,449 | 12/1995 | Pyle . | |
| 5,541,677 | 7/1996 | Huhtala . | |

*Primary Examiner*—Hune X. Dang
*Attorney, Agent, or Firm*—Walker, McKenzie & Walker, PC

[57] ABSTRACT

An eyesight and hearing safety apparatus for use by a human being. The apparatus comprises a front guard portion including a front transparent panel for protecting the eyesight of the human being. The apparatus further comprises a first and a second earplug for protecting the hearing of the human being. The apparatus further comprises a first temple having a first attachment end and a first support end. The first attachment end is hingedly attached to one end of the front guard portion. The first earplug is attached to the first temple adjacent the first support end. The first temple and the first earplug support the front guard portion from a respective auditory canal when the human being is wearing the apparatus. The apparatus further comprises a second temple having a second attachment end and a second support end. The second attachment end is hingedly attached to one end of the front guard portion. The second earplug is attached to the second temple adjacent the second support end. The second temple and the second earplug support the front guard portion from a respective auditory canal when the human being is wearing the apparatus. The first and second temples may be adjustable to horizontally and vertically position the respective earplug for comfortable insertion into the respective auditory canal of the human being.

10 Claims, 3 Drawing Sheets

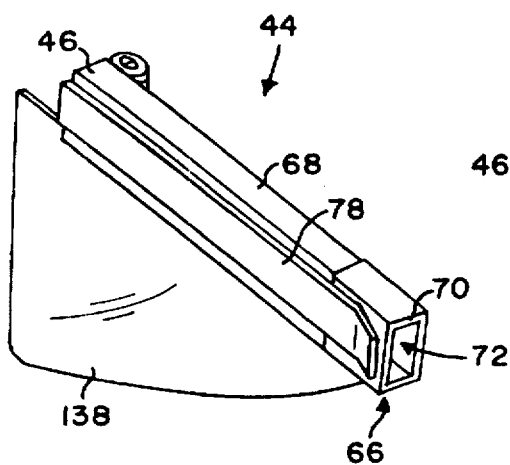
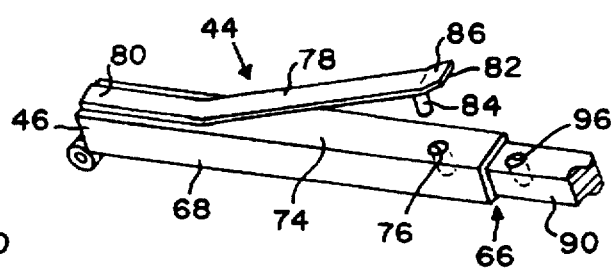
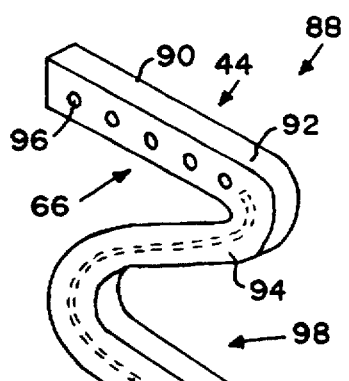
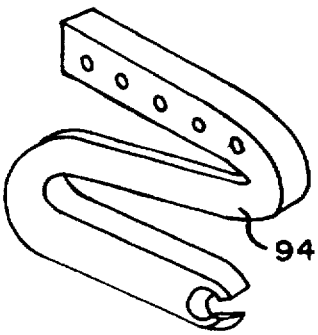
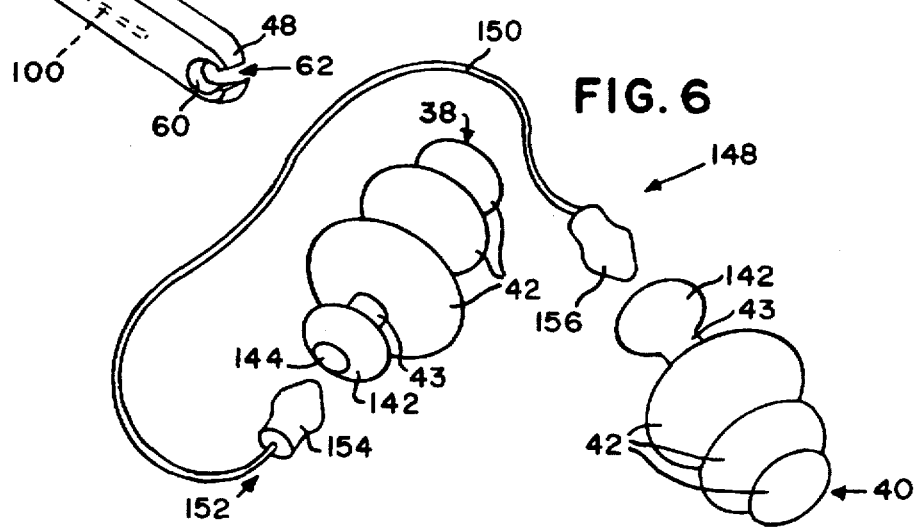

5,781,272

EYESIGHT PROTECTION APPARATUS WITH ATTACHED EARPLUGS

BACKGROUND OF THE INVENTION

1. Field of the Invention

The present invention relates, in general, to safety devices, and in particular, to devices which protect the eyesight and hearing of a human being from injury.

2. Information Disclosure Statement

It is often desired to protect the eyes of a human being from being injured by flying debris at the workplace and to protect the hearing of a human being from being injured due to excessive noise at the workplace. Well-known solutions for this problem include providing separate safety glasses and earplugs. A problem occurs because a human being, such as an employee, can use only one protection device when both are needed for proper protection in the work environment. Other well-known solutions for this problem include providing safety glasses with earplugs attached to the safety glasses in some manner. The problem with these solutions is that a human being can wear the safety glasses without using the earplugs, thus, causing damage to his or her hearing. As an example, Leight, U.S. Pat. No. 3,943,925 provides a hearing protector assembly which can be attached to safety glasses. The protector assembly can be completely removed from the safety glasses, and in addition the assembly includes a brake (70) which can hold the earplug away from the ear.

It is therefore desirable to have an eyesight and hearing safety device which by design requires a human being to use both safety glasses and earplugs, thus, protecting the eyes and the hearing of the human being from harm.

A preliminary patentability search in Class 128, subclasses 864 and 866; Class 351, subclasses 118 and 123; and Class 2, subclass 13, produced the following patents, some of which may be relevant to the present invention: Malcom, U.S. Pat. No. 3,384,903, issued May 28, 1968; Davis, U.S. Pat. No. 3,620,608, issued Nov. 16, 1971; Leight, U.S. Pat. No. 3,943,925, issued Mar. 16, 1976; Walters et al., U.S. Pat. No. 4,153,348, issued May 8, 1979; Andersson, U.S. Pat. No. 4,671,265, issued Jun. 9, 1987; Sonthonnax, U.S. Pat. No. 4,848,892, issued Jul. 18, 1989; Kahaney, U.S. Pat. No. 4,955,708, issued Sep. 11, 1990; Grozil, U.S. Pat. No. 5,074,375, issued Dec. 24, 1991; Pyle, U.S. Pat. No. 5,475,449, issued Dec. 12, 1995; and Huhtala, U.S. Pat. No. 5,541,677, issued Jul. 30, 1996. None of these references, either singly or in combination, disclose or suggest the present invention.

BRIEF SUMMARY OF THE INVENTION

The present invention is an eyesight and hearing safety apparatus for use by a human being. The apparatus comprises a front guard portion, a first and a second earplug, and a first and a second temple. The front guard portion includes a front transparent panel for protecting the eyesight of the human being and a bridge portion for supporting the front guard portion. The front guard portion has a left front guard portion end and a right front guard portion end. The first and second earplugs are for supporting the front guard portion from a respective auditory canal when the human being is wearing the apparatus to protect the eyesight and hearing of the human being. The first temple has a first attachment end and a first support end. The first attachment end is attached to the left front guard portion end. The first earplug is attached to the first temple, adjacent the first support end. The second temple has a second attachment end and a second support end. The second attachment end is attached to the right front guard portion end. The second earplug is attached to the second temple, adjacent said second support end. The bridge portion, the first earplug, and the second earplug provide the only means of supporting the front guard portion when the human being is wearing the apparatus to protect the eyesight and hearing of the human being.

It is an object of the present invention to provide an eyesight and hearing safety apparatus which requires a human being to use both eyesight and hearing protection while wearing the apparatus.

It is a further object of the present invention to provide an eyesight and hearing safety apparatus which can be firmly secured in place so that the human being can be very physically active while wearing the apparatus.

BRIEF DESCRIPTION OF THE SEVERAL VIEWS OF THE DRAWING

FIG. 3 is a perspective view of a portion of a first temple and of a first side transparent panel.

FIG. 4 is a different perspective view of the portion of the first temple shown in FIG. 3.

FIG. 5 is a perspective view of another portion of the first temple shown adjusted to a first vertical position.

FIG. 5A is a perspective view of the other portion of the first temple shown adjusted to a second vertical position.

FIG. 6 is an enlarged perspective view of a first and a second earplug and suspending means.

DETAILED DESCRIPTION OF THE INVENTION

Figure 1:
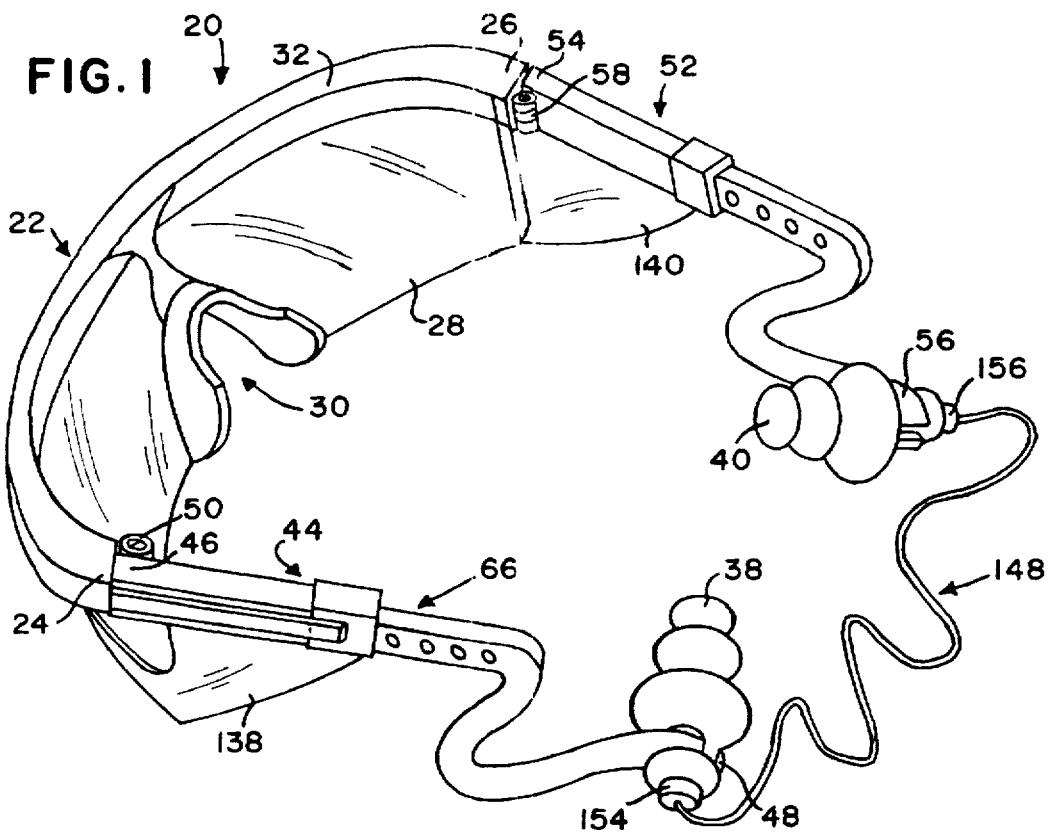
FIG. 1 is a perspective view of the present invention.
Figure 2:
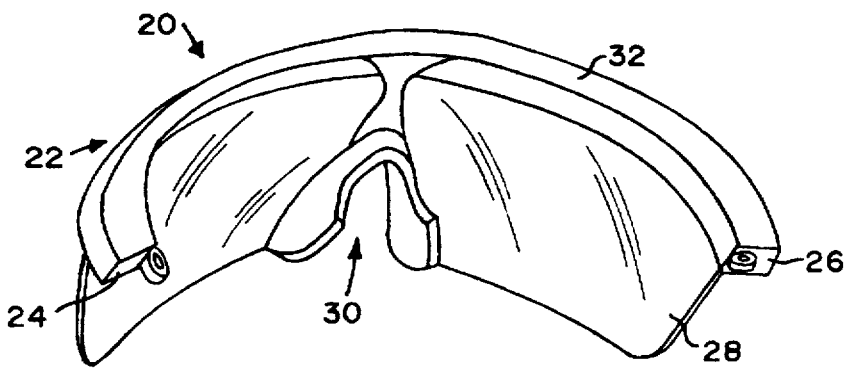
FIG. 2 is a perspective view of the front guard portion.

Referring to FIGS. 1-9A, the present invention is seen to comprise an eyesight and hearing safety apparatus 20. Referring to FIGS. 1 and 2, eyesight and hearing safety apparatus 20 is seen to comprise a front guard portion 22 having a left front guard portion end 24 and a right front guard portion end 26. The front guard portion 22 includes a front transparent panel 28 for protecting the eyesight of a human being. The front transparent panel 28 is preferably constructed from a well known clear plastic material suitable for viewing therethrough. The front guard portion 22 includes a well known bridge portion 30 for supporting the front guard portion 22 on the nose of a human being. The front guard portion 22 preferably includes an elongated resilient member 32. The front transparent panel 28 is disposed adjacent to the elongated resilient member 32 and is preferably attached to the elongated resilient member 32. The elongated resilient member 32 is preferably constructed in the shape of a curve and includes the well known bridge portion 30 depending therefrom. The bottom surface of the elongated resilient member 32 has a first groove (hidden) and the top surface of the bridge portion 30 has a second groove (hidden). The first and second grooves are for securing the front transparent panel 28 as is well known in the art. The elongated resilient member 32 preferably includes the left front guard portion end 24 and the right front guard portion end 26. Further details concerning the construction and operation of the elongated resilient member 32 will be described in a following section.

Referring to FIGS. 1 and 6, the eyesight and hearing safety apparatus 20 is seen to further comprise a first earplug 38 and a second earplug 40 for supporting the front guard portion 22 from a respective auditory canal when the human being is wearing the apparatus 20 to protect the eyesight and hearing of the human being. The first and second earplugs 38, 40 are preferably constructed to each have multiple curved elements 42 for snugly engaging the auditory canal. The diameter of each curved element 42 decreases as the particular curved element 42 is located closer to the end which first engages the auditory canal. Each earplug 38, 40 preferably further includes an attachment stem 43 for attaching the earplugs 38, 40 to the eyesight and hearing safety apparatus 20. Each earplug 38, 40 is preferably constructed from a well known rubber material.

Referring to FIG. 1, the eyesight and hearing safety apparatus 20 is seen to further comprise a first temple 44 having a first attachment end 46 and a first support end 48. The first attachment end 46 is attached to the left front guard portion end 24, preferably by well known hinge means, such as first hinge 50. The first earplug 38 is attached to the first temple 44, preferably adjacent the first support end 48. The first temple 44 is constructed to have a shape so that the first earplug 38 can be inserted into the left auditory canal of the human being and so that the first earplug 38 will support the front guard portion 22 when inserted into the left auditory canal of the human being.

Referring to FIG. 1, the eyesight and hearing safety apparatus 20 is seen to further comprise a second temple 52 having a second attachment end 54 and a second support end 56. The second attachment end 54 is attached to the right front guard portion end 26, preferably by well known hinge means, such as second hinge 58. The second earplug 40 is attached to the second temple 52, preferably adjacent the second support end 56. The second temple 52 is constructed to have a shape so that the second earplug 40 can be inserted into the right auditory canal of the human being and so that the second earplug 40 will support the front guard portion 22 when inserted into the right auditory canal of the human being.

The first and second earplugs 38, 40 and the bridge portion 30 cooperate to support the front guard portion 22 on the head of the human being. The bridge portion 30 supports the front guard portion 22 on the nose of the human being. When inserted into the left auditory canal, the first earplug 38 supports the first temple 44, preferably adjacent the first support end 48. The first temple 44 is attached to the left front guard portion end 24 so that the first earplug 38 supports the left side of the front guard portion 22. Similarly, the second earplug 40 supports the second temple 52, preferably adjacent the second support end 56. The second temple 52 is attached to the right front guard portion end 26 so that the second earplug 40 supports the right side of the front guard portion 22.

Preferably, the first and second temples 44, 52 are formed so that the first and second support ends 48, 56 are laterally displaced towards each other, so that the first and second support ends 48, 56 are displaced lower than the respective first and second attachment ends 46, 54, and so that the first and second support ends 48, 56 are angled slightly upward to facilitate in placing the first 38 and second 40 earplugs into the respective auditory canal of the human being.

Referring to FIGS. 1 and 2, the elongated resilient member 32, preferably allows the front guard portion 22 to flex slightly outward in response to an applied outward pressure while the apparatus 20 is being placed on or removed from the head of the human being. While on the head of the human being, the elongated resilient member 32 creates an inward pressure respectively at the left and right front guard portion ends 24, 26, and this inward pressure is transmitted along the first and second temples 44, 52 to comfortably secure the first and second earplugs 38, 40 in the respective auditory canal. The elongated resilient member 32 is preferably constructed from a well known resilient material, such as, for example, plastic.

Preferably, the bridge portion 30, the first earplug 38, and the second earplug 40 provide the only means of supporting the front guard portion 22 when the human being is wearing the apparatus 20 to protect the eyesight and hearing of the human being. The eyesight and hearing safety apparatus 20 does not require the temples 44, 52 to include portions to support the apparatus 20 on the top of the ears, nor does the apparatus 20 require a strap to support the apparatus 20 around the back of the head of the human being. If the first and second earplugs 38, 40 are removed and the apparatus 20 is worn by the human being, the first and second support ends 48, 56 will apply an uncomfortable pressure against the ears of the human being, thus, deterring wearing of the apparatus 20 without the first and second earplugs 38, 40. Additionally, without the first and second earplugs 38, 40, the front guard portion 22 will not be firmly secured in place as will be the case when the first and second earplugs 38, 40 are inserted into the respective auditory canals of the human being.

Referring to FIGS. 1, 5, and 6 the first temple 44 preferably includes a first means of attaching the first earplug 38 to the first temple 44. The first means of attaching preferably comprises a first aperture 60 extending through the first temple 44 adjacent the first support end 48. The first aperture 60 preferably has a first slot 62 through which the attachment stem 43 of the first earplug 38 can be forced so that it is secured in the first aperture 60. While secured in the first aperture 60, the first earplug 38 is preferably attached to the first temple 44 at a fixed first predetermined location of attachment along a length of the first temple 44. The first earplug 38 is preferably attached to the first temple 44 to have a position which is substantially non-adjustable along the length of the first temple 44 with respect to the first predetermined location of attachment.

Once the first earplug 38 is secured in the first aperture 60, the first earplug 38 can be removed by forcing the attachment stem 43 of the first earplug 38 through the first slot 62 in the opposite direction. The removed first earplug 38 can then be cleaned or replaced as is necessary. The first means of attaching could comprise other well known means for attaching the first earplug 38 to the first temple 44 such as, for, example, a screw or an end plug extending through the first aperture 60 and into the first earplug 38.

Figure 9A:
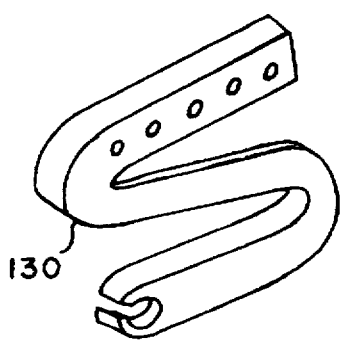
FIG. 9A is a perspective view of the other portion of the second temple shown adjusted to a second vertical position.
Figure 9:
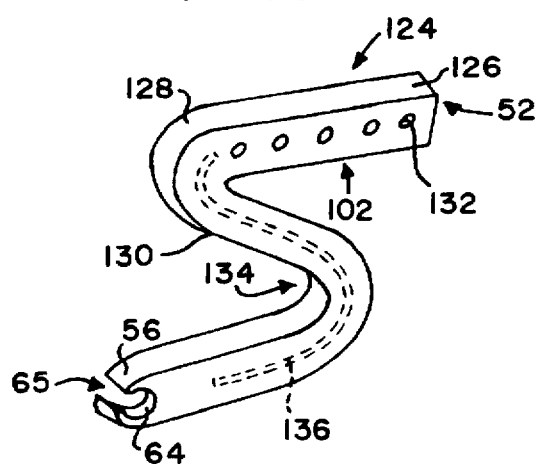
FIG. 9 is a perspective view of another portion of the second temple shown adjusted to a first vertical position.

Referring to FIGS. 1, 6, and 9 the second temple 52 preferably includes a second means of attaching the second earplug 40 to the second temple 52. The second means of attaching preferably comprises a second aperture 64 extending through the second temple 52 adjacent the second support end 56. The second aperture 64 preferably has a second slot 65 through which the attachment stem 43 of the second earplug 40 can be forced so that it is secured in the second aperture 64. While secured in the second aperture 64, the second earplug 40 is preferably attached to the second temple 52 at a fixed second predetermined location of attachment along a length of the second temple 52. The second earplug 40 is preferably attached to the second temple 52 to have a position which is substantially non-adjustable along the length of the second temple 52 with respect to the second predetermined location of attachment.

Once the second earplug 40 is secured in the second aperture 64, the second earplug 40 can be removed by forcing the attachment stem 43 of the second earplug 40 through the second slot 65 in the opposite direction. The removed second earplug 40 can then be cleaned or replaced as is necessary. The second means of attaching could comprise other well known means for attaching the second earplug 40 to the second temple 52 such as, for, example, a screw or an end plug extending through the second aperture 64 and into the second earplug 40.

Referring to FIGS. 1, 3, and 4, the first temple 44 preferably includes first horizontal adjustment means 66 for horizontally adjusting the first earplug 38 to a selected horizontal position. First horizontal adjustment means 66 preferably includes a first front temple portion 68. The first front temple portion 68 has an end which serves as the first attachment end 46 of the first temple 44. The first front temple portion 68 is preferably constructed in the shape of a sleeve having a rectangular cross section. The first front temple portion 68 has a first receiving end 70 and a first channel 72 extending longitudinally from the first receiving end 70 and into the interior of the first front temple portion 68. Referring to FIG. 4, a first outward side 74 of the first front temple portion 68 has a first hole 76 extending therethrough. First horizontal adjustment means 66 preferably further includes a first resilient member 78 having a first resilient member attachment end 80 and a first resilient member tab end 82. The first resilient member attachment end 80 is attached to the first outward side 74 of the first front temple portion 68, adjacent the first attachment end 46. FIG. 3 shows the first resilient member 78 in its normal in-use position, while FIG. 4 shows the first resilient member 78 in a lifted position. The first resilient member 78 includes a first pin 84 which removably extends through the first hole 76. The first resilient member 78 includes a first tab 86 adjacent the first resilient member tab end 82. The first pin 84 can be retracted from the first hole 76 by lifting the first tab 86 away from the first outward side 74 of the first front temple portion 68 as shown in FIG. 4. The first resilient member 78 is constructed from a well known resilient material, such as a resilient plastic or metal.

Referring to FIG. 5, the first temple 44 preferably includes a first rear temple portion 88 including a first arm 90 having a first arm end 92 being connected to a first deformable shape retaining member 94 at the first arm end 92. The first deformable shape retaining member 94 preferably includes the first support end 48 and is attached to the first earplug 38 (shown in FIG. 1). First horizontal adjustment means 66 preferably includes the first arm 90, and the first arm 90 is sized for receipt into the first channel 72 (shown in FIG. 3). The first arm 90 has a first plurality of apertures 96 for selectively receiving the first pin 84 (shown in FIG. 4) to horizontally position the first earplug 38 (shown in FIG. 1). Referring to FIGS. 1, 3, 4, and 5, the horizontal position of the first earplug 38 can be changed by first lifting the first tab 86 to retract the first pin 84 from the first hole 76 and one of the first plurality of apertures 96. Next, the horizontal position of the first earplug 38 can be changed so that another one of the first plurality of apertures 96 is aligned with the first hole 76. Finally, the first tab 86 is released, the first pin 84 is forced into the selected one of the first plurality of apertures 96 by the first resilient member 78, and the first earplug 38 is secured into the selected horizontal position.

Referring to FIGS. 1, 5, and 5A, the first temple 44 preferably includes first vertical adjustment means 98 for vertically adjusting the first earplug 38 to a selected vertical position. First vertical adjustment means 98 preferably includes the first deformable shape retaining member 94 which is selectively adjustable to vertically position the first earplug 38. The first deformable shape retaining member 94 is preferably constructed by including a first wire 100 inside a flexible material, such as a suitable plastic or rubber material. The first deformable shape retaining member 94 is attached to the first arm end 92. The first arm 90 and the first deformable shape retaining member 94 form the first rear temple portion 88 which preferably has a shape substantially in the form of an S or Z. Notably, the first deformable shape retaining member 94 is preferably constructed laterally inwardly with respect to the first arm 90. The first deformable shape retaining member 94 can be can be vertically adjusted to selectively vertically position the first earplug 38 by applying sufficient force to the first deformable shape retaining member 94 in the desired vertical direction. The first deformable shape retaining member 94 will remain in the vertically adjusted position until sufficient force is applied to position the first deformable shape retaining member 94 to a different vertical position. FIGS. 5 and 5A show the first deformable shape retaining member 94 adjusted to two different vertical positions.

Figure 8:
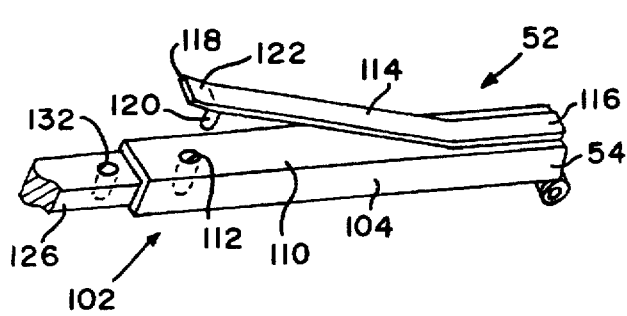
FIG. 8 is a different perspective view of the portion of the second temple shown in FIG. 7.
Figure 7:
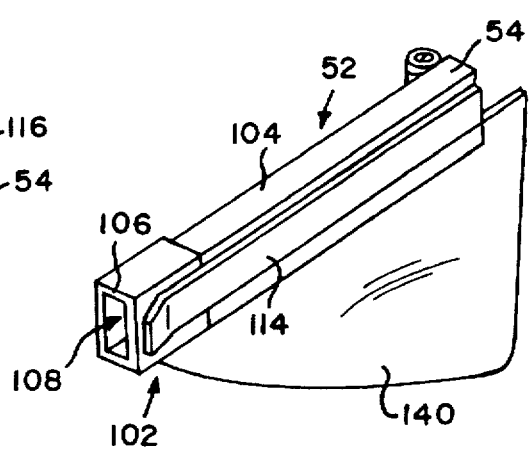
FIG. 7 is a perspective view of a portion of a second temple and of a second side transparent panel.

Referring to FIGS. 1, 7, and 8, the second temple 52 preferably includes second horizontal adjustment means 102 for horizontally adjusting the second earplug 40 to a selected horizontal position. Second horizontal adjustment means 102 preferably includes a second front temple portion 104. The second front temple portion 104 has an end which serves as the second attachment end 54 of the second temple 52. The second front temple portion 104 is preferably constructed in the shape of a sleeve having a rectangular cross section. The second front temple portion 104 has a second receiving end 106 and a second channel 108 extending longitudinally from the second receiving end 106 and into the interior of the second front temple portion 104. Referring to FIG. 8, a second outward side 110 of the second front temple portion 104 has a second hole 112 extending therethrough. Second horizontal adjustment means 102 preferably further includes a second resilient member 114 having a second resilient member attachment end 116 and a second resilient member tab end 118. The second resilient member attachment end 116 is attached to the second outward side 110 of the second front temple portion 104, adjacent the second attachment end 54. FIG. 7 shows the second resilient member 114 in its normal in-use position, while FIG. 8 shows the second resilient member 114 in a lifted position. The second resilient member 114 includes a second pin 120 which removably extends through the second hole 112. The second resilient member 114 includes a second tab 122 adjacent the second resilient member tab end 118. The second pin 120 can be retracted from the second hole 112 by lifting the second tab 122 away from the second outward side 110 of the second front temple portion 104 as shown in FIG. 8. The second resilient member 114 is constructed from a well known resilient material, such as a resilient plastic or metal.

Referring to FIG. 9, the second temple 52 preferably includes a second rear temple portion 124 including a second arm 126 having a second arm end 128 being connected to a second deformable shape retaining member 130 at the second arm end 128. The second deformable shape retaining member 130 preferably includes the second support end 56 and is attached to the second earplug 40 (shown in FIG. 1). Second horizontal adjustment means 102 preferably includes the second arm 126, and the second arm 126 is sized for receipt into the second channel 108 (shown in FIG. 7). The second arm 126 has a second plurality of apertures 132 for selectively receiving the second pin 120 (shown in FIG. 8) to horizontally position the second earplug 40 (shown in FIG. 1). Referring to FIGS. 1, 7, 8, and 9, the horizontal position of the second earplug 40 can be changed by first lifting the second tab 122 to retract the second pin 120 from the second hole 112 and one of the second plurality of apertures 132. Next, the horizontal position of the second earplug 40 can be changed so that another one of the second plurality of apertures 132 is aligned with the second hole 112. Finally, the second tab 122 is released, the second pin 120 is forced into the selected one of the second plurality of apertures 132 by the second resilient member 114, and the second earplug 40 is secured into the selected horizontal position.

Referring to FIGS. 1, 9, and 9A, the second temple 52 preferably includes second vertical adjustment means 134 for vertically adjusting the second earplug 40 to a selected vertical position. Second vertical adjustment means 134 preferably includes the second deformable shape retaining member 130 which is selectively adjustable to vertically position the second earplug 40. The second deformable shape retaining member 130 is preferably constructed by including a second wire 136 inside a flexible material, such as a suitable plastic or rubber material. The second deformable shape retaining member 130 is attached to the second arm end 128. The second arm 126 and the second deformable shape retaining member 130 form the second rear temple portion 124 which preferably has a shape substantially in the form of an S or Z. Notably, the second deformable shape retaining member 130 is preferably constructed laterally inwardly with respect to the second arm 126. The second deformable shape retaining member 130 can be can be vertically adjusted to selectively position the second earplug 40 by applying sufficient force to the second deformable shape retaining member 130 in the desired vertical direction. The second deformable shape retaining member 130 will remain in the vertically adjusted position until sufficient force is applied to position the second deformable shape retaining member 130 to a different vertical position. FIGS. 9 and 9A show the second deformable shape retaining member 130 adjusted to two different vertical positions.

The first and second temples 44, 52 can be adjusted by using the respective horizontal adjustment means 66, 102 and the respective vertical adjustment means 98, 134. In this manner, the first and second earplugs 38, 40 can be positioned to be secured in the auditory canals of human beings with different sized and shaped heads. The eyesight and hearing safety apparatus 20 will be securely held in place and the human being can be very physically active.

Referring to FIGS. 1 and 3, the eyesight and hearing safety apparatus 20 preferably includes a first side transparent panel 138 being disposed adjacent the first temple 44 and preferably being attached to the first front temple portion 68 by means well known in the art. Referring to FIGS. 1 and 7, the eyesight and hearing safety apparatus 20 preferably includes a second side transparent panel 140 being disposed adjacent the second temple 52 and preferably being attached to the second front temple portion 104 by means well known in the art. The first and second side transparent panels 138, 140 are preferably constructed from a well known clear plastic material suitable for viewing therethrough.

Referring to FIG. 6, each earplug 38, 40 preferably includes a ball 142 being attached at one end to the attachment stem 43 and having an earplug aperture 144 at the other end. The earplug aperture 144 leads to a reception cavity (hidden) constructed inside the ball 142.

Referring to FIGS. 1 and 6, the eyesight and hearing safety apparatus 20 preferably includes suspending means 148 for suspending the apparatus 20 from the neck of a human being. Suspending means 148 preferably comprises an elongated securing tiepiece 150. The elongated securing tiepiece 150 is preferably constructed from rubber, but, may be constructed from woven fibers, leather, plastic, or any other well known suitable material. Suspending means 148 includes detaching means 152 for detaching suspending means 148 from the apparatus 20 in response to an applied force. Detaching means 152 preferably comprises a first retaining element 154 attached to one end of the elongated securing tiepiece 150 and a second retaining element 156 attached to the other end of the elongated securing tiepiece 150. The first and second retaining elements 154, 156 are constructed to be removably received into the earplug aperture 144 and reception cavity of each respective earplug 38, 40. When the first and second retaining elements 154, 156 are received in the respective reception cavities, the eyesight and hearing safety apparatus 20 can be removed from the head of the human being, and the human being can suspend the apparatus 20 from his or her neck. If the apparatus 20 should accidentally become caught in a piece of machinery, one or both of the retaining elements 154, 156 will be removed from the respective reception cavity due to the force of the machinery pulling on the apparatus 20. In this manner, injury that could be caused by the machinery is prevented. The first and second retaining elements 154, 156 can be constructed from well known materials such as rubber or plastic.

Although the present invention has been described and illustrated with respect to a preferred embodiment and a preferred use therefor, it is not to be so limited since modifications and changes can be made therein which are within the full intended scope of the invention.

We claim:

1. An eyesight and hearing safety apparatus for use by a human being, said apparatus comprising:

(a) a front guard portion having a left front guard portion end and a right front guard portion end; said front guard portion including:

i. a elongated resilient member, and ii. a front transparent panel being attached to said elongated resilient member, said front transparent panel being for protecting the eyesight of the human being;

(b) a first and a second earplug, said first and second earplugs being for supporting said front guard portion from a respective auditory canal when the human being is wearing said apparatus;

(c) a first temple including:

i. a first sleeve portion having a first attachment end being attached to said left front guard portion end, a first receiving end, and a first hole extending through a first outward side of the first sleeve portion, ii a first resilient member being attached to said first sleeve portion and including a first pin for removably extending through said first hole, iii. a first arm being sized for receipt into said first sleeve portion, said first arm having a first arm end and a first plurality of apertures for selectively receiving said first pin to horizontally position said first earplug, iv a first deformable shape retaining member being selectively adjustable to vertically position said first earplug, said first deformable shape retaining member being attached to the first arm end and including a first support end, said first earplug being attached to said first deformable shape retaining member adjacent said first support end;

(d) a second temple including:
i. a second sleeve portion having a second attachment end being attached to said right front guard portion end, a second receiving end, and a second hole extending through a second outward side of the second sleeve portion, ii a second resilient member being attached to said second sleeve portion and including a second pin for removably extending through said second hole, iii. a second arm being sized for receipt into said second sleeve portion, said second arm having a second arm end and a second plurality of apertures for selectively receiving said second pin to horizontally position said second earplug, iv a second deformable shape retaining member being selectively adjustable to vertically position said second earplug, said second deformable shape retaining member being attached to the second arm end and including a second support end, said second earplug being attached to said second deformable shape retaining member adjacent said second support end;

(e) a first side transparent panel being attached to said first sleeve portion;

(f) a second side transparent panel being attached to said second sleeve portion; and (g) an elongated securing tiepiece removably attached to said first and second earplugs.

2. An eyesight and hearing safety apparatus for use by a human being, said apparatus comprising:

(a) a front guard portion including a front transparent panel for protecting the eyesight of a human being and having a left front guard portion end and a right front guard portion end;

(b) a left temple being attached to said left front guard portion end, said left temple including a substantially fixed-length left shape-retaining member;

(c) a right temple being attached to said right front guard portion end, said right temple including a substantially fixed-length right shape-retaining member; and (d) a left and a right earplug, said left and right earplugs being for supporting said front guard portion from respective left and right auditory canals of the human being when the human being is wearing said apparatus, said left earplug being attached to said left shape-retaining member in fixed relation thereto and said right earplug being attached to said right shape-retaining member in fixed relation thereto.

3. The eyesight and hearing safety apparatus as recited in claim 2, in which said left and right shape-retaining members are deformable.

4. The eyesight and hearing safety apparatus as recited in claim 2, in which said apparatus has no means for supporting said apparatus from the human being's ears other than said left and right earplugs.

5. The eyesight and hearing safety apparatus as recited in claim 2, in which said left and right temples each include means for horizontally adjusting the respective left and right earplugs to respective selected horizontal positions.

6. The eyesight and hearing safety apparatus as recited in claim 2, in which said apparatus further includes a left side transparent panel being disposed adjacent said left temple, and a right side transparent panel being disposed adjacent said right temple.

7. The eyesight and hearing safety apparatus as recited in claim 2, in which said apparatus further includes suspending means for suspending said apparatus from the neck of a human being; said suspending means including an elongated tiepiece having left and right ends and including left and right retaining elements respectively attached to said left and right ends of said elongated tiepiece; said left and right earplugs respectively having left and right cavities thereinto, with said left and right retaining elements being respectively removably received into said left and right cavities.

8. The eyesight and hearing safety apparatus as recited in claim 2, in which said front guard portion further includes an elongated resilient member attached to said front transparent panel for biasing, when the human being is wearing said apparatus, said left and right earplugs respectively inwardly into the left and right auditory canals of the human being.

9. The eyesight and hearing safety apparatus as recited in claim 2, in which said left and right shape-retaining members are deformable; said left and right temples each include means for horizontally adjusting the respective left and right earplugs to respective selected horizontal positions; and said apparatus has no means for supporting said apparatus from the human being's ears other than said left and right earplugs.

10. The eyesight and hearing safety apparatus as recited in claim 9, in which said front guard portion further includes an elongated resilient member attached to said front transparent panel for biasing, when the human being is wearing said apparatus, said left and right earplugs respectively inwardly into the left and right auditory canals of the human being.

* * * * *